United States Patent [19]

Brodasky

[11] 4,213,326

[45] Jul. 22, 1980

[54] SAMPLE SUPPLY DEVICE

[75] Inventor: Thomas F. Brodasky, Oshtemo Township, Kalamazoo County, Mich.

[73] Assignee: The Upjohn Company, Kalamazoo, Mich.

[21] Appl. No.: 12,067

[22] Filed: Feb. 14, 1979

[51] Int. Cl.² .......................................... G01N 31/08
[52] U.S. Cl. ..................................... 73/23.1; 250/288
[58] Field of Search ................... 73/23.1, 23, 422 GC, 73/61.1 C; 250/288, 281

[56] References Cited

U.S. PATENT DOCUMENTS 3,997,298  12/1976  McLafferty et al. ......... 73/61.1 C X

*Primary Examiner*—Gerald Goldberg
*Assistant Examiner*—Joseph W. Roskos

*Attorney, Agent, or Firm*—Blanchard, Flynn, Thiel, Boutell & Tanis

[57] ABSTRACT

A sample introduction device for introducing a vaporized sample to the ion source of a mass spectrometer of a combined gas chromatography-mass spectrographic (GC/MS) apparatus. The sample introduction device replaces the jet separator of the GC/MS apparatus. The sample introduction device includes a sample holding tube which is releasably attachable to the isolation valve between the gas chromatography column and the mass spectrometer of the GC/MS apparatus. The sample introduction device includes means for connecting the sample holding tube to a vacuum source by means of a valve so that the sample holding tube can be evacuated prior to connecting the sample holding tube through the isolation valve to the ion source of the mass spectrometer.

13 Claims, 4 Drawing Figures

U.S. Patent
Jul. 22, 1980
4,213,326
FIG. 1
PRIOR ART
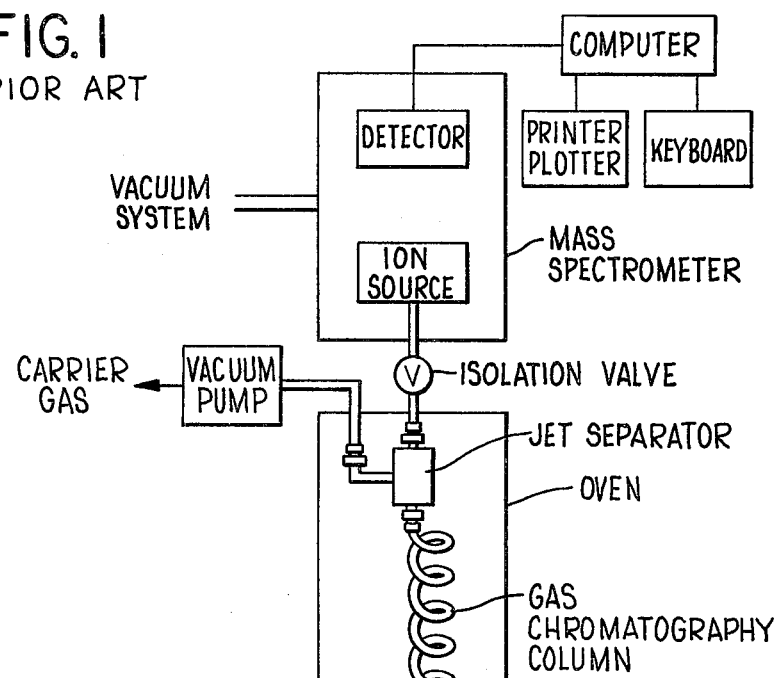
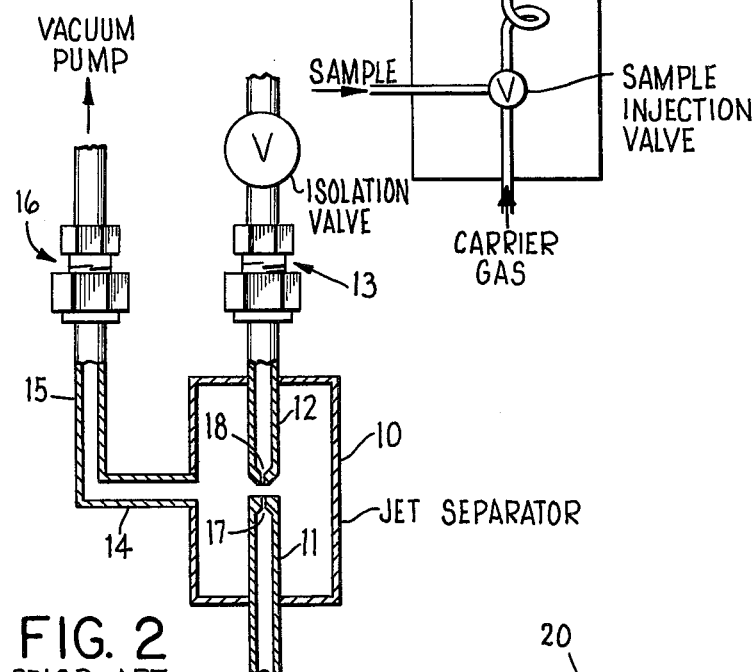
FIG. 2
PRIOR ART
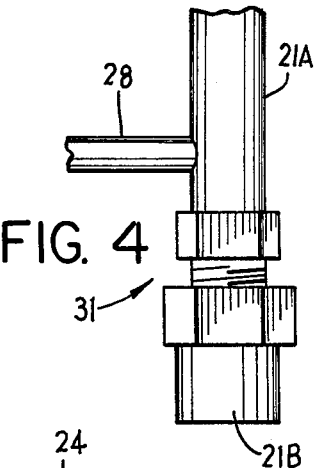
FIG. 4
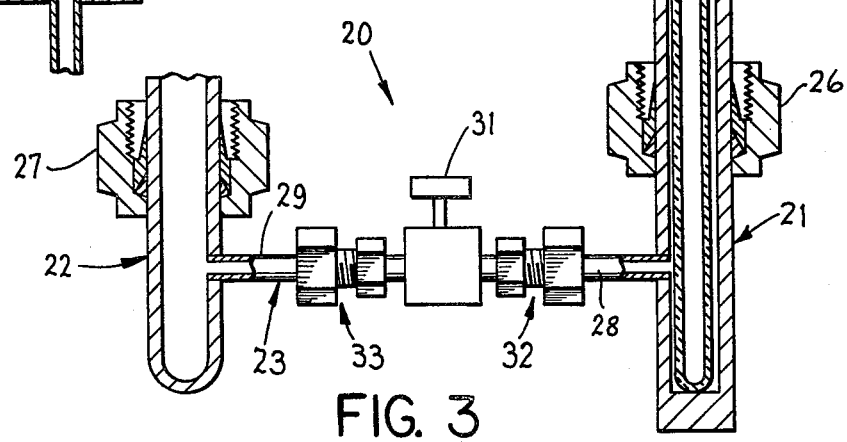
FIG. 3

SAMPLE SUPPLY DEVICE

This invention relates to a device for introducing a vaporized sample directly into the ion source of the mass spectrometer portion of a combined gas chromatography-mass spectrographic apparatus.

Combined gas chromatography-mass spectrographic apparatuses, which are hereinafter referred to as GC/MS systems, are widely used in the field of analytical chemistry. The gas chromatography column portion of the GC/MS system is used to separate volatile pure compounds, or certain volatile fractions, from a starting mixture. The gaseous sample discharged from the gas chromatography column is flowed into the ion source of the mass spectrometer portion of the GC/MS system so that mass spectrum analysis of the sample can be performed. It also is known to bypass the gas chromatography column portion of the GC/MS system by introducing the sample directly to the ion source of the mass spectrometer portion of the GC/MS system. This direct introduction technique can be used, for example, to analyze samples which are not sufficiently volatile to be eluted from a gas chromatography column or to analyze samples which already are pure.

Many GC/MS systems have been built by connecting a gas chromatography to a separate mass spectrometer by means of appropriate conduits and control mechanisms. In such GC/MS systems, the provision of a device for effecting direct sample introduction to the ion source of the mass spectrometer portion is not difficult because there can be used the direct sample introduction mechanisms that are conventionally used in mass spectrometers per se. However, such GC/MS systems are relatively expensive and bulky. They also have been complex to operate for various reasons, including the need to manually adjust the operating parameters of the GC/MS system to obtain the best test results.

A compact integrated GC/MS system has recently become commercially available. The compact integrated GC/MS system is considerably smaller than prior art GC/MS systems and it is of sufficiently small size that it can be placed on a bench top or desk top so that it is more convenient for laboratory use. One specific compact integrated GC/MS system is comprised of a programmable desk-top calculator and a GC/MS unit. The operating parameters of the GC/MS unit are controlled by the calculator. Also, the calculator provides a digital and/or graphical print-out of the mass spectrum data detected by the detector of the mass spectrometer.

A schematic illustration of a compact integrated GC/MS unit is shown in FIG. 1. As shown in FIG. 1, in normal operation a sample to be analyzed is injected into the gas chromatography column by means of the sample injection valve. The sample is picked up by the carrier gas and molecules of the sample are flowed, together with the carrier gas, through the gas chromatography column wherein the components of the sample are separated in accordance with conventional gas chromatography techniques. In the jet separator, the carrier gas is separated from the molecules of the sample and the carrier gas is removed by a vacuum pump. The jet separator, the gas chromatography column and the sample injection valve are all contained in an oven, in accordance with conventional practice. The molecules of the sample, separated from the carrier gas in the jet separator, then flow through the isolation valve which are located between the gas chromatography column and the mass spectrometer. The molecules of the sample then flow to the ion source of the mass spectrometer and they are subjected to mass spectrographic analysis in a conventional manner. The detector in the mass spectrometer provides an electrical output signal which is transformed to a digital and/or graphical representation in the printer-plotter, under the control of the keyboard-controlled computer.

In FIG. 2, there is shown a partial cross section of the jet separator portion of the apparatus of FIG. 1 and its associated connections. The jet separator comprises a housing 10 defining an enlarged internal chamber. The discharge end 11 of the gas chromatography column extends into the housing 10 from one end thereof. A conduit 12 extends into the housing from the opposite end thereof. The conduit 12 is connected by a suitable fitting 13, such as a SWAGELOK fitting, to the isolation valve. Another conduit 14 extends sidewardly from the housing and it has an upwardly extending leg 15 which is connected to the vacuum pump by means of a suitable fitting 16, such as a SWAGELOK fitting.

The discharge end portion 11 of the gas chromatography column and the lower end of the conduit 12 have coaxial openings 17 and 18 of very small diameter, which openings are coaxial and are located close to each other. Because of their heavier mass, the molecules of the sample flow substantially in a straight line in the space between the openings 17 and 18 so that many of the molecules of the sample discharged from opening 17 flow into opening 18 and thence into and through the conduit 12 to the isolation valve, and thence into the ion source of the mass spectrometer. On the other hand, because of the lighter mass of the carrier gas, significant amounts of the carrier gas do not flow into the opening 18, but rather, the carrier gas flows into the chamber in the housing 10 and it is removed therefrom by operation of the vacuum pump.

A commercially available GC/MS system of the type shown in FIGS. 1 and 2 is identified as HP Model 5992A, available from Hewlett-Packard Company of Palo Alto, Calif.

The GC/MS system shown in FIGS. 1 and 2 does not include mechanism for directly introducing a sample to the ion source of the mass spectrometer. As a consequence, the GC/MS system shown in FIGS. 1 and 2 is limited to use for analyzing samples which are sufficiently volatile that they can be eluted from the gas chromatography column. This is a significant limitation on the practical laboratory use of this GC/MS system, because it cannot be used for the analysis of many kinds of samples, even though the mass spectrometer portion of this GC/MS system is otherwise capable of being effectively used for analyzing a wide variety of samples, including less volatile samples which cannot be eluted from the gas chromatography column portion thereof.

The known direct sample introduction devices used in mass spectrometers per se are not convenient for use in the GC/MS system of FIGS. 1 and 2 because those devices are too complex and expensive, and because major physical alteration of the construction of the mass spectrometer portion of the FIGS. 1 and 2 GC/MS system would be required in order to add thereto the known direct sample introduction devices. This would increase greatly the cost and/or the size of the FIGS. 1 and 2 GC/MS system which is not desired because the FIGS. 1 and 2 GC/MS system is intended to be a compact unit which is lower in cost than other previously known GC/MS systems. For example, the use of a known sample probe which communicates directly with the ion source, together with the required vacuum lock structure that is needed with such a direct sample probe, are not fully satisfactory for use in the FIGS. 1 and 2 GC/MS system for the above-described reasons. Thus, there exists a need for a sample introduction device which can be conveniently added to a GC/MS system of the type shown in FIGS. 1 and 2 and which will make it possible to provide for direct introduction of samples to the mass spectrometer portion of that GC/MS system.

Accordingly, it is an object of this invention to provide a device for introducing samples directly into the ion source of the mass spectrometer portion of a GC/MS system of the type shown in FIGS. 1 and 2, which sample introduction device can easily be added to or removed from the GC/MS system as the need arises and which will not significantly alter the intended normal mode of operation of the mass spectrometer portion thereof.

It is a further object of this invention to provide a sample introduction device, as aforesaid, which is installed in place of the jet separator of the GC/MS system of the type shown in FIGS. 1 and 2.

It is a further object of this invention to provide a sample introduction device, as aforesaid, in which the vacuum existing in the mass spectrometer is employed to transport volatilized sample directly to the ion source of the mass spectrometer so that less volatile samples can be directly fed to the ion source of the mass spectrometer without using the gas chromatography column.

It is a further object of this invention to provide a sample introduction device, as aforesaid, in which heat from the heaters of the diffusion pump in the mass spectrometer and/or heating of the oven of the gas chromatography column are used to volatilize the sample.

It is a further object of this invention to provide a sample introduction device, as aforesaid, in which the vacuum pump conventionally used in the gas chromatography column to remove the carrier gas from the sample, can additionally be used to evacuate the sample holder of the sample introduction device, according to the invention, before the isolation valve is opened, whereby to minimize disruption of the vacuum in the mass spectrometer and thereby make possible more rapid operation.

It is a further object of this invention to provide a sample introduction device, as aforesaid, which is of simple structure, which is inexpensive to manufacture, which is easy to install and which is effective in operation.

According to the invention, there is provided a sample introduction device for introducing an evaporated sample to the ion source of the mass spectrometer portion of a combined GC/MS system. The sample introduction device, according to the invention, comprises a sample holding tube adapted to replace the jet separator of the gas chromatography column and adapted to be releasably sealingly connected to the isolation valve between the gas chromatography column and the mass spectrometer. The sample holding tube holds a sample present in a non-gaseous state. The sample is volatilized by heat supplied from the heaters of the diffusion pump of the mass spectrometer and/or by heat supplied from the oven in which the gas chromatography column is placed. The sample holding tube has a fitting member thereon which is adapted to be releasably secured to a cooperating fitting member on the isolation valve, which fitting member on the isolation valve is normally directly connected to a fitting member on the jet separator. After the isolation valve is opened and when the sample contained in the sample holding tube is evaporated therein, the vacuum present in the mass spectrometer is effective to transport the evaporated sample to the ion source of the mass spectrometer.

The sample introduction device according to the invention preferably also includes a conduit which extends from the sample holding tube and is adapted to be releasably sealingly connected to the vacuum source for the jet separator of the gas chromatography column whereby air can be evacuated from the sample present in the sample holding tube prior to opening the isolation valve. A vacuum control valve is provided in the conduit in order to open and close communication between the vacuum source of the jet separator of the gas chromatography column and the sample holding tube. The entirety of the sample introduction device is adapted to be mounted at the discharge end of the gas chromatography column, in place of the jet separator normally present thereat, whereby the sample holding tube can be evacuated and the sample therein can be transformed to the vapor state and then flowed through the isolation valve to the ion source of the mass spectrometer.

BRIEF DESCRIPTION OF THE DRAWINGS

FIG. 1 is a schematic view of a prior art compact integrated GC/MS system, in which the sample introduction device according to the invention can be used;

FIG. 2 is an enlarged, partially sectional view of the jet separator portion of the prior art GC/MS system of FIG. 1;

FIG. 3 is an enlarged partially sectional view of the sample introduction device according to the invention; and FIG. 4 is a view of a fragment of a modification of the sample introduction device according to the invention.

DETAILED DESCRIPTION OF THE PREFERRED EMBODIMENT

Referring to FIG. 3, the sample introduction device 20, according to the present invention, is comprised of a pair of upright, parallel, elongated tubes 21 and 22 which are interconnected adjacent their lower ends by means of a conduit assembly 23. The elongated tube 21 is open at its top and closed at its bottom. The tube 21 functions as a sample holder, that is, it functions to hold the sample that is to be vaporized and then fed through the isolation valve to the ion source of the mass spectrometer. The sample can be contained in a capillary tube 24 which is slidably receivable into the tube 21 through the open upper end thereof. The capillary tube 24 is closed at its bottom and is open at its top so that a sample can be placed therein. There is sufficient clearance between the external wall of the capillary tube 24 and the internal wall of the tube 21 and between the upper end of tube 21 and the male portion of fitting 13 that the below-described vacuum source is effective to remove air from the space between the tube 21 and the capillary tube 24 and also from the interior of the capillary tube.

In one specific embodiment of the invention, the sample holder tube 21 has an inside diameter of 2 millimeters, an outside diameter of 10 millimeters and a length of 10.5 centimeters.

A suitable fitting member 26, such as a SWAGELOK female nut fitting member, is provided on the exterior of the sample holder tube 21 so that said fitting member can be rotated as well as moved axially on the tube 21 for threaded interconnection with the cooperating male member of fitting 13 on the isolation valve as shown in FIG. 2, whereby the sample holder tube 21 can be releasably sealingly connected to the isolation valve.

The tube 22 also is closed at its bottom and open at its top. The tube 22 has a suitable fitting member 27, such as a SWAGELOK female fitting, mounted on the exterior thereof for rotation and for axial movement thereon. Thus, the fitting 27 can be releasably sealingly connected to the corresponding male member of fitting 16 associated with the vacuum pump as shown in FIG. 2, whereby the tube 22 can be releasably sealingly connected to the vacuum pump.

In one specific embodiment of the invention, the tube 22 has an inside diameter of 7 mm, an outside diameter of 10 mm and a length of 5 mm. In this embodiment, the fitting members 26 and 27 can be of identical size.

Thus, the fittings 26 and 27 make it possible to use the sample introduction device 20, according to the invention, in place of the jet separator that normally is located at the discharge end of the gas chromatography column, simply by unscrewing the fitting members on the jet separator and removing it, and then placing the sample introduction device 20, according to the invention, in place thereof and assembling the fitting members 26 and 27 of the sample introduction device, according to the invention, to the fitting members on the isolation valve and the vacuum pump.

The transverse conduit assembly 23 is comprised of conduits 28 and 29 which are respectively secured to the tubes 21 and 22 adjacent the lower ends thereof. The mutually remote ends of the conduits 28 and 29 thus communicate directly with the interiors of the tubes 21 and 22. The adjacent ends of the conduits 28 and 29 are connected to a valve 31 in any suitable manner, such as by means of SWAGELOK fittings 32 and 33, or by silver soldering or the like. The valve 31 is here shown as being manually operable and it can, for example, be a needle valve. The valve 31, when open, communicates the interior of the tube 21 via the conduits 28 and 29 and tube 22 to the vacuum source of the gas chromatography column so that a vacuum can be drawn inside the sample holding tube 21 and, when used, also inside the capillary tube 24.

In one specific embodiment of the invention, the conduits 28 and 29 have an inside diameter of 2 mm and an outside diameter of 3 mm.

The foregoing parts of the sample introduction device 20, according to the invention, are made of materials capable of withstanding temperatures of up to 350° C. and suitable for mass spectrometry operations, such as stainless steel, glass and the like.

In use, the jet separator of the GC/MS system of FIGS. 1 and 2 and its associated conduits and fitting members are removed from their normal position connected to the gas chromatography column, the vacuum pump and the isolation valve. At this time, the isolation valve is closed so that the mass spectrometer unit is isolated, whereby the very high vacuum present therein can be effectively maintained. Also, at this time, the sample injection valve of the gas chromatography column is closed and the vacuum pump for the jet separator is turned off. A small quantity of a sample to be analyzed by mass spectrometry is placed in a capillary tube 24 and then the capillary tube is inserted in the sample holder tube 21 of the sample introduction device 20, according to the invention. The sample introduction device 20 is then attached to the isolation valve fitting member and to the fitting member of the vacuum pump of the gas chromatography column by threading the fitting members 26 and 27 on the tubes 21 and 22 onto the corresponding fitting members of the isolation valve and the vacuum pump. The fittings are tightened so as to establish a fluid-tight connection of the sample introduction device 20 to the isolation valve and the vacuum pump. The vacuum pump is then turned on and the valve 31 is opened, whereby to place the sample holder tube 21 and the interior of the capillary tube 24 therein in communication with tube 22 and the vacuum pump so that the interior of the sample introduction device, including the capillary tube, is evacuated. This takes only a few moments. After air has been evacuated from the sample introduction device 20, the valve 31 is closed and the isolation valve is opened. Also, the filaments in the mass spectrometer portion are turned on to monitor ion current and to monitor any single ion mass that is desired. The vacuum existing in the mass spectrometer is effective to transport volatilized molecules of the sample present in the capillary tube 24 to the ion source of the mass spectrometer. Because of the fact that the isolation valve is closed until the sample holder has been evacuated by operation of the vacuum pump of the gas chromatography column, disruption of the vaccum in the mass spectrometer unit is minimized so that proper mass spectrometer conditions can be achieved rapidly inside the mass spectrometer unit.

The heat for volatilizing the sample present in the capillary tube 24 can be obtained by heat transfer from the diffusion pump heaters present in the mass spectrometer. Such heat transfer occurs by direct heat conduction through the isolation valve and associated conduits and fittings directly to the sample introduction device 20. In many cases, the heat thus transmitted from the diffusion pump heaters is sufficient to volatilize the sample. However, if the amount of heat thus transferred to the sample is insufficient to volatilize the sample, additional heat can be supplied by heating the oven of the gas chromatography column, it being noted that the sample introduction device 20 is located inside that oven. In this fashion, the sample can be heated at a programmed rate by programmed heating operation of the oven extending from ambient temperatures up to a temperature of about 350° C.

The sample introduction device 20, according to the invention, has been used to carry out mass spectrum analysis of a variety of samples that could not effectively be analyzed by feeding them to the inlet of the gas chromatography column because of their insufficient volatility. The results of operations carried out using the sample introduction device 20, according to the invention, in an HP Model 5992A GC/MS system were compared with the results obtained using an Atlas CH7 mass spectrometer having a direct probe inlet. The test results showed that both types of apparatus provided closely similar spectra, thus showing that the use of the sample introduction device 20, according to the invention, is effective for the direct introduction of a sample to be analyzed directly to the ion source of the mass spectrometer portion of the FIGS. 1 and 2 GC/MS unit.

MODIFICATION

Referring to FIG. 4, a modified sample introduction device is disclosed therein. It comprises a modified sample holding tube 21A in which the lower end thereof is removably closed by a cup-shaped cap 21B which is releasably sealingly connected to the remainder of the tube by means of a fitting 31. In this embodiment, the sample is placed into the internal recess in the cap 21B which is then secured to the lower end of the tube 21A by tightening the nut of the fitting. In this embodiment, it is possible to analyze samples in succession without disassembling the remainder of the sample introducing device from the vacuum pump and the isolation valve. This permits more rapid analysis of a plurality of samples by direct sample introduction to the ion source of the mass spectrometer portion of the FIGS. 1 and 2 GC/MS unit.

Although particular preferred embodiments of the invention have been described above, the invention contemplates such changes or modifications therein as lie within the scope of the following claims.

The embodiments of the invention in which an exclusive property or privilege is claimed are defined as follows:

1. A sample introduction device for introducing a vaporized sample to the ion source of a mass spectrometer, with there being an isolation valve for controlling flow of vaporized sample to said ion source and a vacuum source separate from said mass spectrometer for removing air from the sample, said sample introduction device comprising:
    a sample holding tube for holding a sample in a non-gaseous state, said sample holding tube having on the exterior thereof a fitting member adapted to be releasably sealingly secured to a cooperating fitting member of said isolation valve so that the sample contained in said sample holding tube can be vaporized therein and transported through said isolation valve to said ion source of said mass spectrometer; and
    conduit means releasably sealingly connectable to said vacuum source and connected to said sample holding tube whereby air can be evacuated from said sample holding tube, and a vacuum control valve in said conduit means for opening and closing communication between said vacuum source and said sample holding tube.

2. A sample introduction device as claimed in claim 1 in which said conduit means comprises a second tube having a fitting member on the exterior thereof adapted to be releasably sealingly secured to a cooperating fitting member of said vacuum source.

3. A sample introduction device as claimed in claim 2 in which said sample holding tube and said second tube are upright, straight, substantially parallel tubes which are closed at their bottoms and open at their tops, the fitting members on said tubes being mounted on the upper portions of said tubes, said conduit means comprising a transverse conduit extending between and communicating at its ends with said tubes close to the lower ends thereof and below the fitting members thereon, said vacuum control valve being mounted in said transverse conduit.

4. A sample introduction device as claimed in claim 3 in which the external diameter of said tubes are the same and the sizes of said fitting members thereon are the same, said fitting members comprising rotatable and axially movable female fitting members adapted to receive corresponding male fitting members associated with the vacuum source and the isolation valve.

5. A sample introduction device according to claim 3 in which said sample holding tube has an integral end wall at the bottom thereof.

6. A sample introduction device according to claim 3 in which said sample introduction tube comprises a removable cap at the lower end thereof for holding a sample therein.

7. In combination with a gas chromatography-mass spectrographic apparatus comprising an oven, a gas chromatography column disposed inside said oven, said gas chromatography column having a sample inlet valve at one end thereof for admitting a sample and carrier gas into said one end of said column, said gas chromatography column having a jet separator at the other end thereof for separating molecules of the sample from the carrier gas, said jet separator having first and second conduits extending therefrom, a vacuum source adapted to be connected to said first conduit of said jet separator for removing said carrier gas, said second conduit being adapted for receiving and transporting molecules of said sample from said gas chromatography column, a mass spectrometer disposed outside said oven, an isolation valve connected to the ion source of said mass spectrometer and adapted to control supply of a test sample to the ion source of said mass spectrometer, said isolation valve having a fitting member associated therewith and adapted to be releasably sealingly connected to a cooperating fitting member on said second jet separator conduit, said vacuum source having a fitting member associated therewith and adapted to be releasably sealingly connected to a corresponding fitting on said first jet separator conduit, the improvement which comprises:
    a sample holding tube for holding a sample in a non-gaseous state, said sample holding tube being disposed in said oven and having a fitting member releasably sealingly secured to said fitting member of said isolation valve so that the sample contained in said sample holding tube can be vaporized therein and transported through said isolation valve to said ion source of said mass spectrometer, said sample holding tube being connected to the fitting member of said isolation valve in place of said second jet separator conduit.

8. The combination of claim 7, including conduit means releasably sealingly connected to said vacuum source and connected to said sample holding tube for evacuating air from said sample holding tube, and a vacuum control valve in said conduit means for opening and closing communication between said vacuum source and said sample holding tube.

9. The combination of claim 8 in which said conduit means comprises a second tube having a fitting member on the exterior thereof releasably sealingly secured to said fitting member of said vacuum source.

10. The combination of claim 9 in which said sample holding tube and said second tube are upright, straight, substantially parallel tubes which are closed at their bottoms and open at their tops, the fitting members on said tubes being mounted on the upper portions of said tubes, said conduit means comprising a transverse conduit extending between and communicating at its ends with said tubes close to the lower ends thereof and below the fitting members thereon, said vacuum control valve being mounted in said transverse conduit.

11. The combination of claim 10 in which the external diameters of said tubes are the same and the sizes of said fitting members thereon are the same, said fitting members comprising rotatable and axially movable female members adapted to receive corresponding male fitting members associated with said vacuum source and said isolation valve.

12. The combination of claim 10 in which said sample holding tube has an integral non-removable end wall at the bottom thereof.

13. The combination of claim 10 in which said sample introduction tube comprises a removable cap at the lower end thereof for holding a sample therein.

* * * * *